United States Patent
Borrelli et al.

(10) Patent No.: US 6,663,865 B1
(45) Date of Patent: Dec. 16, 2003

(54) TUMOR NECROSIS FACTOR ANTAGONISTS AND THEIR USE IN ENDOMETRIOSIS

(75) Inventors: Francesco Borrelli, Rome (IT); Mauro D'Antonio, Caserta (IT); Fabrizio Martelli, Rome (IT)

(73) Assignee: Applied Research Systems ARS Holding N.V., Curacao (AN)

(*) Notice: Subject to any disclaimer, the term of this patent is extended or adjusted under 35 U.S.C. 154(b) by 0 days.

(21) Appl. No.: 09/889,828

(22) PCT Filed: Jan. 19, 2000

(86) PCT No.: PCT/IB00/00052
§ 371 (c)(1),
(2), (4) Date: Sep. 14, 2001

(87) PCT Pub. No.: WO00/43031
PCT Pub. Date: Jul. 27, 2000

(30) Foreign Application Priority Data

Jan. 22, 1999 (EP) .............................. 99101194

(51) Int. Cl.⁷ ...................... A61K 39/395; A61K 39/00
(52) U.S. Cl. .............................. 424/158.1; 424/145.1; 424/184.1; 514/2
(58) Field of Search .......................... 514/2; 424/145.1, 424/158.1, 184.1

(56) References Cited

U.S. PATENT DOCUMENTS 6,423,713 B1 * 7/2002 Anantanarayan et al. 514/235.8

OTHER PUBLICATIONS

Arici A, Oral E, Bukulmez O, Duleba A, Olive DL, Jones EE: The effect of endometriosis on implantation: results from the Yale University in vitro fertilization and embryo transfer program. Fertil.Steril. 1996; 65: 603–607.

Arici A, Tazuke SI, Attar E, Kliman HJ, Olive DL: Interleukin–8 concentration in peritoneal fluid of patients with endometriosis and modulation of interleukin–8 expression in human mesothelial cells. Mol.Hum.Reprod. 1996; 2: 40–45.

Arici A, Oral E, Attar E, Tazuke SI, Olive DL: Monocyte chemotactic protein–1 concentration in peritoneal fluid of women with endometriosis and its modulation of expression in mesothelial cells. Fertil.Steril. 1997; 67: 1065–1072.

Barbieri RL: New therapy for endometriosis. N.Engl.J.Med. 1988; 318: 512–514.

Baxter, A. D. and Montana, J. G. Peptidyl Compounds Having MMP and TNF Inhibitory Activity. Chiroscience Ltd. (WO9806696), Feb. 19, 1998.

Bazzoni F, Beutler B: The tumor necrosis factor ligand and receptor families. N.Engl.J.Med. 1996; 334: 1717–1725.

Cheung AN: Oncogenes and other growth factors in gynaecological neoplasms. Curr.Opin.Obstet.Gynecol. 1996; 8: 46–51.

Daddona, P. E., Ghrayeb, J., Knight, D. M., Le, J., Siegel, S. A., and Vilcek, J. Monoclonal and chimeric antibodies to human TNF—useful for treating sepsis syndrome, cachexia, microbial infections, rheumatoid arthritis, inflammation, etc. Univ New York Medical Cent and Centocor, Inc. (WO9216553), Oct. 1, 1992.

Dawood MY: Considerations in selecting appropriate medical therapy for endometriosis. Int.J.Gynaecol.Obstet. 1993; 40 Suppl:S29–42: S29–42.

Eisermann J, Gast MJ, Pineda J, Odem RR, Collins JL: Tumor necrosis factor in peritoneal fluid of women undergoing laparoscopic surgery. Fertil.Steril. 1988; 50: 573–579.

Eisermann J, Register KB, Strickler RC, Collins JL: The effect of tumor necrosis factor on human sperm motility in vitro. J.Androl. 1989; 10: 270–274.

Fiers W: Tumor necrosis factor. Characterization at the molecular, cellular and in vivo level. FEBS Lett. 1991; 285: 199–212.

Gray PW, Aggarwal BB, Benton CV, et al: Cloning and expression of cDNA for human lymphotoxin, a lymphokine with tumour necrosis activity. Nature 1984; 312: 721–724.

Hahn DW, Carraher RP, Foldesy RG, McGuire JL: Experimental evidence for failure to implant as a mechanism of infertility associated with endometriosis. Am.J.Obstet.Gynecol. 1986; 155: 1109–1113.

Halme J: Role of peritoneal inflammation in endometriosis–associated infertility. Ann.N.Y.Acad.Sci. 1991; 622:266–74: 266–274.

Harada T, Yoshioka H, Yoshida S, et al: Increased interleukin–6 levels in peritoneal fluid of infertile patients with active endometriosis. Am.J.Obstet.Gynecol. 1997; 176: 593–597.

Ho HN, Wu MY, Yang YS: Peritoneal cellular immunity and endometriosis. Am.J.Reprod.Immunol. 1997; 38: 400–412.

Hornung D, Ryan IP, Chao VA, Vigne JL, Schriock ED, Taylor RN: Immunolocalization and regulation of the chemokine RANTES in human endometrial and endometriosis tissues and cells. J.Clin.Endocrinol.Metab. 1997; 82: 1621–1628.

Hunt JS, Chen HL, Hu XL, Tabibzadeh S: Tumor necrosis factor–alpha messenger ribonucleic acid and protein in human endometrium. Biol.Reprod. 1992; 47: 141–147.

(List continued on next page.)

*Primary Examiner*—Lorraine Spector
*Assistant Examiner*—Eileen B. O'Hara
(74) *Attorney, Agent, or Firm*—Browdy and Neimark, PLLC

(57) ABSTRACT

Tumor necrosis factor antagonists are administered in therapeutically effective doses to treat and/or prevent endometriosis. The antagonists of this invention typically are selected from among several classes but preferably are soluble TNF receptors. The antagonists are useful for the regression of endometriotic lesions and, if combined with other active ingredients, for amelioration of related disorders, like infertility.

6 Claims, 3 Drawing Sheets

OTHER PUBLICATIONS

Jacobs, C. A. and Smith, C. A. Treating TNF mediated inflammatory diseases with TNF antagonist—esp. soluble form of TNF receptor, opt. as fusion protein with human immunoglobulin Fc region, esp. for treating arthritis. Immunex Corp. (WO9406476), Mar. 31, 1994.

Koninckx PR, Meuleman C, Demeyere S, Lesaffre E, Cornillie FJ: Suggestive evidence that pelvic endometriosis is a progressive disease, whereas deeply infiltrating endometriosis is associated with pelvic pain. Fertil.Steril. 1991; 55: 759–765.

Koninckx PR, Martin D: Treatment of deeply infiltrating endometriosis. Curr.Opin.Obstet.Gynecol. 1994; 6: 231–241.

MacSween RNM: Muir's Textbook of pathology. Whaley K., 1993; 1024–1025.

Malinak LR, Buttram VCJ, Elias S, Simpson JL: Heritage aspects of endometriosis. II. Clinical characteristics of familial endometriosis. Am.J.Obstet.Gynecol. 1980; 137: 332–337.

Matalliotakis I, Neonaki M, Zolindaki A, Hassan E , Georgoulias V, Koumantakis E: Changes in immunologic variables (TNF–a, sCD8 and sCD4) during danazol treatment in patients with endometriosis. Int.J.Fertil.Womens.Med. 1997; 42: 211–214.

Mori H, Nakagawa M, Itoh N, Wada K, Tamaya T: Danazol suppresses the production of interleukin–1 beta and tumor necrosis factor by human monocytes. Am.J.Reprod.Immunol. 1990; 24: 45–50.

Nophar Y, Kemper O, Brakebusch C, et al: Soluble forms of tumor necrosis factor receptors (TNF–Rs). The cDNA for the type I TNF–R, cloned using amino acid sequence data of its soluble form, encodes both the cell surface and a soluble form of the receptor. EMBO J. 1990; 9: 3269–3278.

Overton C, Fernandez–Shaw S, Hicks B, Barlow D, Starkey P: Peritoneal fluid cytokines and the relationship with endometriosis and pain. Hum.Reprod. 1996; 11: 380–386.

Pennica D, Nedwin GE, Hayflick JS, et al: Human tumour necrosis factor: precursor structure, expression and homology to lymphotoxin. Nature 1984; 312: 724–729.

Rana N, Braun DP, House R, Gebel H, Rotman C, Dmowski WP: Basal and stimulated secretion of cytokines by peritoneal macrophages in women with endometriosis. Fertil.Steril. 1996; 65: 925–930.

Revelli A, Modotti M, Ansaldi C, Massobrio M: Recurrent endometriosis: a review of biological and clinical aspects. Obstet.Gynecol.Surv. 1995; 50: 747–754.

Roby KF, Laham N, Hunt JS: Cellular localization and steroid hormone regulation of mRNA encoding tumour necrosis factor receptor I in mouse uterus. J.Reprod.Fertil. 1996; 106: 285–290.

Shalaby MR, Laegreid WW, Ammann AJ, Liggitt HD: Tumor necrosis factor–alpha–associated uterine endothelial injury in vivo. Influence of dietary fat. Lab.Invest. 1989; 61: 564–570.

Shalaby MR, Sundan A, Loetscher H, Brockhaus M, Lesslauer W, Espevik T: Binding and regulation of cellular functions by monoclonal antibodies against human tumor necrosis factor receptors. J.Exp.Med. 1990; 172: 1517–1520.

Waller KG, Shaw RW: Gonadotropin–releasing hormone analogues for the treatment of endometriosis: long–term follow–up. Fertil.Steril. 1993; 59: 511–515.

Zhang RJ, Wild RA, Ojago JM: Effect of tumor necrosis factor–alpha on adhesion of human endometrial stromal cells to peritoneal mesothelial cells: an in vitro system. Fertil.Steril. 1993; 59: 1196–1201.

* cited by examiner

TUMOR NECROSIS FACTOR ANTAGONISTS AND THEIR USE IN ENDOMETRIOSIS

The present application is the national stage under 35 U.S.C. 371 of international application PCT/IB00/00052, filed Jan. 19, 2000 which designated the United States, and which international application was published under PCT Article 21(2) in the English language.

FIELD OF THE INVENTION

Tumor necrosis factor antagonists are administered in therapeutically effective doses to treat and/or prevent endometriosis. The antagonists of this invention typically are selected among various classes of molecules but preferably are soluble TNF receptors. The antagonists are useful for the regression of endometriotic lesions and, if combined with other active ingredients, for amelioration of related disorders, like infertility.

BACKGROUND OF THE INVENTION

Endometriosis is a female genital disease characterized by the presence of endometrial glands and stroma outside of the endometrial cavity and uterine musculature. The anatomical sites most often affected are the ovaries, uterosacral ligaments, pelvic peritoneum, rectovaginal septum, cervix, vagina, the fallopian tubes and vulva. Generally endometriosis is likely to infiltrate deeply from the rectovaginal sectum in the underlying tissues and not be visible superficially. Occasionally, foci of endometriosis can be encountered in extraovarian sites, like in lungs, bladder, skin, pleura and lymphnodes. Endometriotic lesions are progressive: they are first seen as clear vescicles, which then become red and then progress to black, fibrotic lesions over a period of few years (MacSween, 1993).

Endometriosis is considered as a benign disease, but endometriotic lesions become occasionally malignant. As in other kind of malignancies, the development of endometriosis-derived neoplasms is due to concurrent events, involving alterations in growth factors and/or oncogenes regulation (Cheung, 1996).

Endometriosis is among the most common gynaecological diseases, with prevalence among reproductive age women: this disease is found in about 5–10% of women in reproductive age (Barbieri, 1988). Endometriotic tisssue is completely dependent on estrogen for continued growth, also in ectopic locations. Consequently, endometriosis is rare before menarche and after menopause, when women are deficient in estrogen. Endometriosis hormonal sensitivity is underlying some of the more common symptoms, which are pelvic pain and dysmenorrhea.

Endometriosis is originated from endometrial cells disseminated from uterus to other locations, where viable cells can implant and grow. Two possible mechanisms have been proposed to explain the initial cell spreading. Retrograde menstruation, a common phenomenon among cycling women, makes possible to endometrium-detached fragments to reach, through menstrual reflux liquid, nearby structures in the genital apparatus. Alternatively, to explain the occurrence of endometriosis in sites other than genital structures, endometrial cells may be spread through uterine veins and extension through the lymphatic system (haematogenous or lymphatic dissemination). Also gynaecological surgery can contribute to this spreading (MacSween, 1993).

Apart from endometrial cells dissemination, other factors, such as genetic predisposition (Malinak et al, 1980), as well as immunological alterations (Ho et al., 1997) may determine women's susceptibility to endometriosis. Since endometrial cells are frequently seen in peritoneal fluid in all women at the time of menses, mammalians should have mechanisms, most probably related to immune system, to avoid the onset of endometriosis In general, endometrial cells that escape the host's immune response and have adequate estrogenic stimulation can proliferate to form large, macroscopically visible lesions. Endometriosis is therefore considered as a dynamic process where new lesions are continuously being formed while existing lesions may grow or be destroyed by the host's immune response.

The inflammatory reaction, normally associated to endometriosis, changes the peritoneal environment, since there is an increased volume of peritoneal fluid and peritoneal macrophages are increased in both number and activity. Therefore, monocyte/macrophage system has been proposed as having a key role in the development of endometriosis. Secretory products of macrophages, including RANTES (Hornung et al., 1997), Interleukin-6 (Harada et al., 1997), Interleukin-8 (Arici et al., 1996a), Tumor Necrosis Factor-alpha (Overton et al., 1996), Monocyte Chemotactic Protein-1 (Arici, et al., 1997), were found at higher concentration in the peritoneal fluid of women affected by this disease. Immunological changes have been demonstrated in women with endometriosis but it has not been demonstrated whether these events are responsible for the endometriosis or are a result of the inflammation caused by endometriosis (Rana et al., 1996).

The knowledge about endometriosis, and its relevance for other disorders, is still now limited, even at diagnostic level. Although endometriosis is considered as a major cause of infertility, studies on the pathophysiology of the disease are contradictory and not definitive. There is a poor correlation between the degree of pain or infertility and the severity of disease, since the early lesions are more metabolically active. The infertility rate is higher than the normal population and studies in rabbits have shown that surgical induction of endometriosis leads to a decrease in fertility from 75% to 25% (Hahn et al., 1986). Patients with pelvic pain were found to have endometriosis 71% of the time, while 84% of patients with pelvic pain and infertility had endometriosis diagnosed (Koninckx, et al., 1991). In general, infertility can be found when endometriosis is so extended to disrupt normal vaginal structure, meanwhile pregnancy rates are normal when endometriosis is minimal.

Endometriosis can affect fertility also in a different way. White blood cell messengers, like Interleukin-6, Interferon and Tumor Necrosis Factor, are all increased, adversely affecting oocyte-sperm interaction. Serum samples obtained from women with endometriosis were found to be embryotoxic in mouse embryo models and to inhibit sperm mobility in vitro (Halme, 1991), an effect enhanced when recombinant Tumor Necrosis Factor-alpha is added (Eisermann, 1989). Those studies, however, did not address the problem on how cytokines affect the progression of endometriosis but only showed the effects of such molecules on the viability of germ and embryonic cells.

Hormonal therapy and surgery are the two therapeutic modalities currently used to treat endometriosis. Current pharmacological therapy for endometriosis requires hormonal suppression of the production of estrogen, so that the poor hormone environment blocks the growth of ectopic tissue. Regarding the treatment of endometriosis-related infertility, hormone therapy in patients with minimal disease is of no proven benefit, meanwhile other studies showed an increase in pregnancy rates (Arici et al., 1996b).

Hormonal therapies have included high dose of progestogens, combinations of estrogen and progesterone (using high dose oral contraceptive pills, or OCPs, in a "pseudopregnancy" regimen), Danazol (an androgenic derivative of ethisterone) and more recently GnRH agonists. These hormonal therapies are effective on pelvic pain and induce an objective regression of lesions, but have several caveats. Estrogen may stimulate and cause proliferation of endometriotic tissue since it may be unable to respond to progesterone, even at high doses so that OCPs may offer partial relief to a limited number of patients (Dawood, 1993). Progestational agents can provoke irregular bleeding (50%) along with depression, weight gain, acid fluid retention. Danazol, suppresses endometriosis evoking various responses, including the reduction of soluble Tumor Necrosis Factor alpha, Interleukin-1 beta and CD8 levels in serum (Matalliotakis, 1997; Mori, 1990), the inhibition of de novo steroidogenesis and displacement of estradiol from its receptor. Danazol can improve symptoms in approximately 66–100% of the patients suffering from pain, but crude recurrence rates after up to 4 years are approximately 40%–50%. Other drawbacks of Danazol therapy are weight gain and androgenic side effects, which can cause up to 80% of patients to abandon this therapy (Barbieri, 1988). GnRH analogs are more potent and long acting than native GnRH, which work by removing the estrogenic stimulus for the growth of all estrogen sensitive tissues. Side effects of GnRH analogs are mainly secondary to the profound hypoestrogenemia, like decreased bone density, and recurrence rate are up to 50% after 5 years (Waller and Shaw, 1993).

Depending on the degree of disease, surgical intervention can be conservative, if fertility is desired, or can lead to the removal of the uterus, tubes and ovaries in case of severe disease. In any case, even limited surgical treatment leads to a significant decrease in fertility. Pregnancy rates following surgery generally range between 35% and 65%, so patients need ovulation induction and intrauterine insemination to achieve normal fecundity (Koninckx and Martin, 1994). Clinical reports shows that, after laparotomy and resection of endometriosis, up to 40% of patients required re-operation within 5 years. Even after aggressive surgical intervention recurrence of pain from endometriosis continues to be a significant problem. Some of the reasons for the failure of surgical therapy may include incomplete resection with lesions either not being recognized or missed completely. Many lesions are microscopic and would not be able to be visualized despite the magnification afforded by the laparoscope. Therefore, surgery alone cannot be expected to cure this disease (Revelli et al., 1995).

Since so many patients with endometriosis suffer from the drawbacks of traditional therapies (including hormonal disequilibrium consequences, high recurrency rates and infertility). It is therefore of interest to provide alternative treatments for endometriosis. A possible therapeutic approach may be represented by the use of immunomodularory molecules which could be able to ameliorate both endometriotic lesions and immunological situation. Such an approach has been considered feasible for the treatment of general symptoms (Rana et al., 1996) but there are no experimental evidences pointing our which cytokine, amongst the ones with altered levels of expression following endometriosis, could be a preferred target for the therapeutical intervention.

As previously said, one of the several macrophage secretory products involved in endometriotic inflammatory reaction is Tumor Necrosis Factor (abbreviated, from now on, as TNF). TNF also defined as Cachectin, is a pleiotropic cytokine released by activated T cells and macrophages. TNF is a member of the Interferon, Interleukin and Colony Stimulating Factor cytokine network, which has a key role in signaling system with regard to the pathogenesis of many infectious and inflammatory diseases by inducing a number of proinflammatory changes, including production of other cytokine and adhesion molecule (Fiers, 1991).

For convenience, the term TNF collectively shall mean, in the entire text of the present application, both Tumor Necrosis Factor-alpha or -beta from animals or humans, together with naturally occurring alleles thereof TNF-alpha (Pennica et al., 1984). TNF-beta, also named as lymphotoxin, has a similar activity but is produced by different cell types (lymphocytes and Natural Killer cells) in response to antigenic or mitogenic stimuli (Gray et al., 1984).

TNF is expressed as a mature 17 kDa protein that is active as a trimer. This complex exerts its biological activity by aggregating their cell surface receptors, which mediate specific effects in different organs and tissues. In endometrium, TNF expression is site- and menstrual cycle-dependent (Hunt et al., 1992), and induces apoptosis in endometrium of experimental animals (Shalaby et al., 1989). The adherence of endometrial stromal cells to mesothelial cells was significantly increased by pretreatment of mesothelial cells with TNF (Zhang. et al., 1993), thus supporting the idea that TNF might contribute to the initiation and/or development of endometriosis.

TNF exerts its activity, which is required for the normal development and function of immune system, by binding a family of membrane bound receptor molecules including p55 TNF receptor I, defined in the literature also TNF-RI, and p75 TNF receptor, defined in the literature also TNF-RII (Bazzoni and Beutler, 1996). The dominance of TNF-RI in transducing TNF signal is suggested by the ability of agonist antibodies specific for this receptor to mimic the majority of TNF induced responses (Shalaby et al., 1990). By binding to its membrane-bound receptors, TNF triggers the signaling pathway through cytoplasmic mediators like TRADD and TRAP-1 (for TNF-RI) or TRAF-1 and TRAF-2 (for TNF-RII), leading to different cell response, like T cell proliferation, tumor-cell lysis in vitro, dermal necrosis, insuline resistance, apoptosis. The extracellular portions of both TNF receptors can be shed and these soluble receptors retain the ability to bind TNF, inactivating TNF activity by formation of high affinity complexes, thereby reducing the binding of TNF to target cell membrane receptors (Nophar et al., 1990).

In endometrium, membrane-bound TNF receptors levels are affected by the administration of oestradiol and/or progesterone, resulting in a temporal and cell type-specific expression of TNF-RI in mouse (Roby et al., 1996). However, this study, like many other studies conducted in various models related to endometriosis did not give any hints on the real in vivo effect of TNF and TNF-RI, either membrane-bound or soluble, in the development of endometriotic foci but only a description of the endometriosis-associated immunological abnormalities.

SUMMARY OF THE INVENTION

Present Patent Application is based on the assumption that a TNF antagonist is able, by sequestering circulating TNF, to block the progression of endometriotic lesions. This assumption is confirmed by the finding reported in the example, showing that a TNF antagonist significantly reduces the size of the endometriotic-like foci in a rat experimental model. As a result of applicant's finding, a method is provided herein to treat and/or prevent endometriosis in an individual comprising the administration of a therapeutically effective amount of TNF antagonist.

In a second embodiment, the invention relates to a method for treating and/or preventing endometriosis-related conditions of infertility in an individual comprising the administration of a therapeutically effective amount of TNF antagonist in combination with other drugs.

A still further object of the present invention is the use of a TNF antagonist together with a pharmaceutically acceptable carrier in the preparation of pharmaceutical compositions for treatment of endometriosis.

In the present invention, administration of TNF antagonist can be parenteral or other effective formulations. Any mode of parenteral administration may be suitable including intravenous, intramuscular and subcutaneous. Besides the pharmaceutically acceptable carrier, the composition of the invention can also comprise minor amounts of additives, such as stabilizers, excipients, buffers and preservatives.

TNF antagonists useful in the method of the present invention include soluble TNF receptor molecules, anti-TNF antibodies and compounds which prevent and/or inhibit TNF receptor signaling. It is possible to use the TNF antagonist alone or in combination with other TNF antagonists. The combination with one or more pharmaceutically active products is also possible, in particular to ameliorate conditions of patients suffering from endometriosis-related infertility.

DESCRIPTION OF THE INVENTION

The invention described herein clearly shows the unexpected result that sequestering TNF (which is only one of the several cytokines whose level of expression is increased in peritoneal fluid following endometriosis) by means of a TNF antagonist, reduces endometriotic-like foci in a rat experimental model. This model demonstrates also that such effect is obtained without affecting significantly the hormonal equilibrium and Natural Killer cells activity. The reduction of endometriotic lesions using TNF antagonists can also improve fertility rates, since the normalization of genital structure has a positive effect on the implantation rate.

Therefore, the main object of the present invention is to provide a method to treat and/or prevent endometriosis in an individual comprising administering a therapeutically effective amount of TNF antagonist.

In a second embodiment, the invention relates to a method for treating endometriosis-related conditions of infertility in an individual comprising the administration of a therapeutically effective amount of TNF antagonist in combination with other drugs.

A still further object of the present invention is the use of a TNF antagonist together with a pharmaceutically acceptable carrier in the preparation of pharmaceutical compositions for treatment and/or prevention of endometriosis. The pharmaceutical compositions prepared in this way are also a further object of the present invention.

The active ingredients of the claimed compositions herein are TNF antagonists. Claimed TNF antagonists exert their activity in one of two ways. First, antagonists can bind to or sequester the TNF molecule itself with sufficient affinity and specificity to substantially neutralize the TNF epitope responsible for TNF receptor binding (hereinafter termed "sequestering antagonists"). Alternatively, TNF antagonists can inhibit TNF signaling pathway activated by the cell surface receptor after TNF binding (hereinafter termed "signaling antagonists"). Both groups of antagonists are useful, either alone or together, in the therapy of endometriosis, according to the present invention.

TNF antagonists are easily identified and rated by routine screening of candidates for their effect on the activity of native TNF on susceptible cell lines in vitro, for example human B cells, in which TNF causes proliferation and Ig secretion. The assay contains TNF formulation at varying dilutions of candidate antagonist, e.g. from 0.1 to 100 times the molar amount of TNF used in the assay, and controls with no TNF or only antagonist (Tucci et al., 1992).

Sequestering antagonists are the preferred TNF antagonists according to the present invention. Amongst sequestering antagonists, those polypeptides that bind TNF with high affinity and possess low immunogenicity are preferred. Soluble TNF receptor molecules and neutralizing antibodies to TNF are particularly preferred. For example, TNF-RI and TNF-RII are useful in the present invention. Truncated forms of these receptors, comprising the extracellular domains of the receptors or functional portions thereof, are more particularly preferred antagonists according to the present invention. Truncated forms of the TNF receptors are soluble and have been detected in urine and serum as 30 kDa and 40 kDa TNF inhibitory binding proteins, which were originally called respectively TBPI and TBPII (Engelmann et al., 1990). Derivatives, fragments, regions and functional portions of the receptor molecules functionally resemble the receptor molecules that can be used in the present invention. Such functional equivalent or derivative of the receptor molecule refers to the portion of the said polypeptide, or of the sequence encoding the receptor molecule, that is of sufficient size and able to bind TNF with such an affinity that the interaction with the membrane-bound TNF receptor is inhibited or blocked. In preferred embodiment, human soluble TNF-RI is the TNF antagonist to be administered to patients. The natural and recombinant soluble TNF receptor molecules and methods of their production have been described in the European Patent Applications EP 308,378, EP 398,327 and EP 433,900

TNF receptor multimeric molecules and TNF immunoreceptor fusion molecules, and derivatives or portions thereof, are additional examples of receptor molecules useful in the methods of the present invention. TNF receptor multimeric molecules useful in the present invention comprise all or a functional portion of the extracellular domain of two or more TNF receptors linked via one or more polypeptide linkers. The multimeric molecules can further comprise a signal peptide of a secreted protein to direct expression of the multimeric molecule. These multimeric molecules and methods of their production have been described in the European Patent Application EP 526,905.

TNF immunoreceptor fusion molecules useful in the methods of the present invention comprise at least one portion of one or more immunoglobulin molecules and all or a functional portion of one or more TNF receptors. These immunoreceptor fusion molecules can be assembled as monomers, or hetero- or homo-multimers. The immunoreceptor fusion molecules can also be monovalent or multivalent. TNF immunoreceptor fusion molecules and methods for their production have been described in the European Patent Application EP 620,739, corresponding to PCT Patent Application WO 94/06476.

Another class of sequestering antagonists useful in the method of the present invention is represented by the anti-TNF antibodies, including monoclonal, chimeric humanized, and recombinant antibodies and fragment thereof which are characterized by high affinity binding to TNF in vivo and low toxicity. The antibodies which can be used in the invention are characterized by their ability to treat patients for a period sufficient to have good to excellent regression of endometriotic lesions, alleviation of symptoms and low toxicity. Neutralizing antibodies are readily raised in animals such as rabbits or mice by immunization with TNF. Immunized mice are particularly useful for providing sources of B cells for the manufacture of hybridomas, which in turn are cultured to produce large quantities of anti-TNF monoclonal antibodies. Chimeric antibodies are immunoglobulin molecules characterized by two or more segments or portions derived from different animal species. Generally, the variable region of the chimeric antibody is derived from a non human mammalian antibody, such as murine monoclonal antibody, and the immunoglobulin constant region is derived from a human immunoglobulin molecule. Preferably, both regions and the combination have low immunogenicity as routinely determined (Elliott et al., 1994). Humanized antibodies are immunoglonbulin molecules created by genetic engineering techniques in which the murine constant regions are replaced with human counterparts while retaining the murine antigen binding regions. The resulting mouse-human chimeric antibody should have reduced immunogenicity and improved pharmacokinetics in humans (Knight et al., 1993). Preferred examples of high affinity monoclonal antibodies and chimeric derivatives thereof, useful in the methods of the present invention, are described in the European Patent Application EP 186,833 and PCT Patent Application WO 92/16553.

TNF antagonist can be administered to an individual in a variety of ways. The routes of administration include intradermal, transdermal (e.g. in slow release formulations), intramuscular, intraperitoneal, intravenous, subcutaneous, oral, epidural, topical, and intranasal routes. Any other therapeutically efficacious route of administration can be used, for example absorption through epithelial or endothelial tissues or by gene therapy wherein a DNA molecule encoding the TNF antagonist is administered to the patient (e.g. via a vector) which causes the TNF antagonist to be expressed and secreted in vivo. In addition the TNF antagonist can be administered together with other components of biologically active agents such as pharmaceutically acceptable surfactants, excipients, diluents or any other carrier.

The definition of "pharmaceutically acceptable" is meant to encompass any carrier, which does not interfere with effectiveness of the biological activity of the active ingredient and that is not toxic to the host to which it is administered. For example, for parenteral administration, TNF antagonist may be formulated in a unit dosage form for injection in vehicles such as saline, dextrose solution, serum albumin and Ringer's solution.

For parenteral (e.g. intravenous, subcutaneous, intramuscular) administration, TNF antagonists can be formulated as a solution, suspension, emulsion or lyophilized powder in association with a pharmaceutically acceptable parenteral vehicle (e.g. water, saline, dextrose solution) and additives that maintain isotonicity (e.g. mannitol) or chemical stability (e.g. preservatives and buffers). The formulation is sterilized by commonly used techniques.

The bioavailability of the TNF antagonist can be also ameliorated by using conjugation procedures which increase the half-life of the molecule in human body, for example linking the molecule to Polyethylenglycol, as described in the PCT Patent Application WO 92/13095.

The therapeutically effective amounts of TNF antagonist will be a function of many variables, including the type of antagonist, the affinity of the antagonist for TNF, any residual cytotoxic activity exhibited by the antagonists, the route of administration, the clinical condition of the patient (including the desirability of maintaining a non-toxic level of endogenous TNF activity), the presence of multiple TNF combining sites in sequestering agents, e.g. antibodies.

A "therapeutically effective amount" is such that when administered, the TNF antagonist results in inhibition of the biological activity of TNF. The dosage administered, as single or multiple doses, to an individual will vary depending upon a variety of factor, including TNF antagonist pharmacokinetic properties, the route of administration, patient conditions and characteristics (sex, age, body weight, health, size), extent of symptoms, concurrent treatments, frequency of treatment and the effect desired. Adjustment and manipulation of established dosage ranges are well within the ability of those skilled, as well as in vitro and in vivo methods of determining the inhibition of TNF in an individual.

Since the maximum tolerated dose of TNF in human clinical trials has ranged up to about 25 micrograms/m$^2$ body surface/24 hrs, the amount of antagonist administered generally needs not exceed a dose which is calculated to neutralize this amount of TNF. Accordingly, the molar dose of TNF antagonist will vary about from 0.001 to 10 times the maximum tolerated molar dose of TNF, although as noted above this will be subject to a great deal of therapeutic discretion.

Moreover, the data obtained in clinical studies, wherein the increase of the concentration of TNF in peritoneal fluid in women with endometriosis was demonstrated using various protocols (Eisermann et al., 1988; Halme, 1991; Overton et al., 1996), can be also useful in the determination of the TNF antagonist effective dose to be administered Usually a daily dosage of active ingredient can be about 0.01 to 100 milligrams per kilogram of body weight. Ordinarily 1 to 40 milligrams per kilogram per day given in divided doses or in sustained release form is effective to obtain the desired results. Second or subsequent administrations can be performed at a dosage which is the same, less than or greater than the initial or previous dose administered to the individual. A second or subsequent administrations can be administered during or prior to relapse of the endometriosis or the related symptoms. The terms "relapse" or "reoccurrence" are defined to encompass the appearance of one or more of symptoms of endometriosis.

The TNF antagonist can be administered prophylactically or therapeutically to an individual prior to, simultaneously or sequentially with other therapeutic regimens or agents (e.g. multiple drug regimens), in a therapeutically effective amount, in particular for the treatment of infertility. TNF antagonists that are administered simultaneously with other therapeutic agents can be administered in the same or different compositions. In particular, when infertility is the endometriosis associated disorder intended to be cured, biologically active human chorionic gonadotrophin (hCG), luteinizing hormone (LH) or follicle stimulating hormone (FSH), either in a natural highly purified or in a recombinant form, can be administered. Such molecules and methods of their production have been described in the European Patent Applications EP 160,699, EP 211,894 and EP 322,438.

The present invention will now be illustrated by the example, which is not intended to be limiting in any way, and makes reference to the following figures.

DESCRIPTION OF THE FIGURES

FIG. 1 shows the effects of Antide (2 mg/kg, subcutaneous given every 3 days), recombinant soluble TNF-RI (10 mg/kg, s.c. given into two daily doses over a 1-week period) on the size of engraftments in rats with experimental endometriosis 2 days and 9 days after the last treatment. These data, which are obtained using 6 animals/group for the first sacrifice time-point and 5 animals/group for the second sacrifice time-point, represent the mean percentage of inhibition ±SEM.

Figure 2:
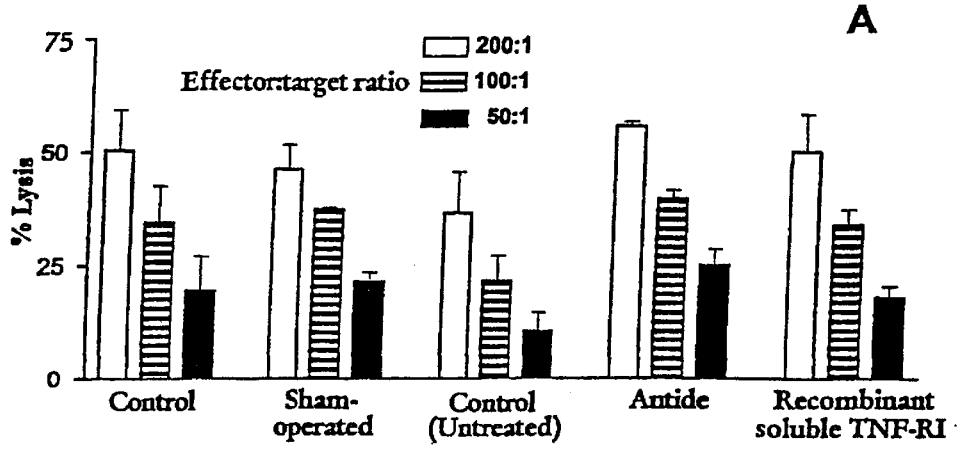
Figure 2:
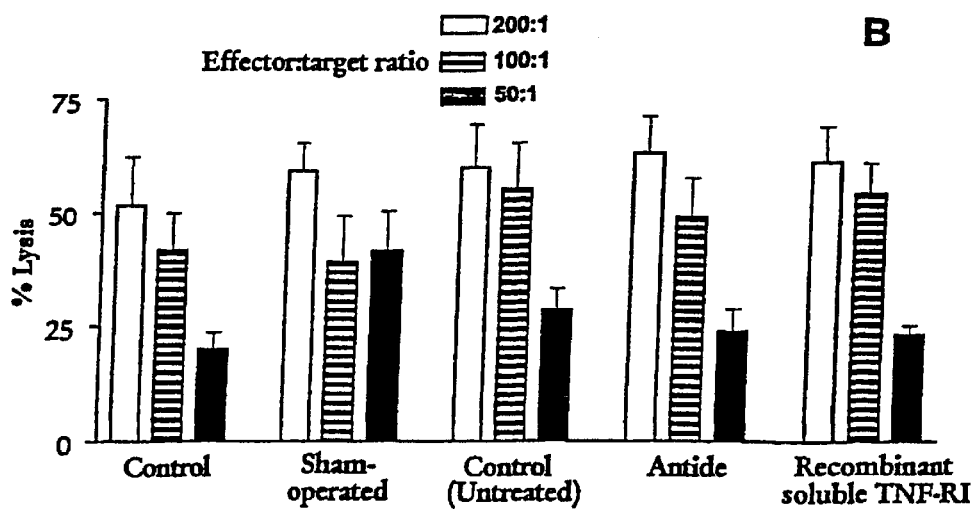

FIGS. 2A and B shows the effects of recombinant soluble TNF-RI (10 mg/kg s.c. given in two daily doses over a 1-week period) and Antide (2 mg/kg s.c. given every 3 days) on the rat NK activity of rat spleen cells against YAC cells ($^{51}$Cr release) 2 days (panel A) and 9 days after the last treatment (panel B). Data represent mean percentage of lysis ±SEM.

Figure 3:
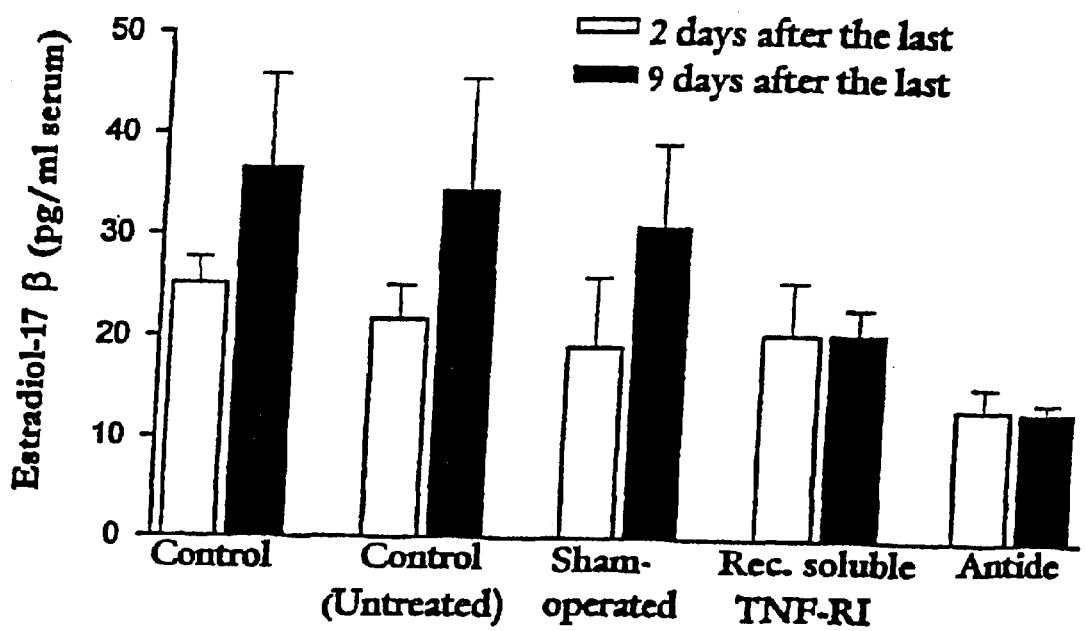

FIG. 3 shows the effects of recombinant soluble TNF-RI (10 mg/kg s.c. given in two daily doses over a 1-week period) as compared to control and Antide (2 mg/kg s.c. given every 3 days) on estradiol-17β serum levels on experimental endometriosis in rats. Data represent mean concentration of estradiol-17β ±SEM.

EXAMPLE

Materials and Methods

Animals. Female Sprague-Dawley rats (250–275 g) were purchased from Charles River Italia (Calco, Lecco, Italy). The animals were housed under the following environmental conditions: temperature 22±2° C., relative humidity 55±10%, ventilation 15±3 air changes per hour filtered on HEPA 99.997% filters and artificial lighting with a circadian cycle of 12 hours of light (7:00–19:00). Before the experiments the animals were allowed to acclimatize to these conditions for a period of at least one week. The animals were fed ad libitum by a standard pellet diet.

Study drugs. Antide was prepared and provided by Bachem, (California, USA). Human recombinant soluble TNF-RI molecule used in the example has a sequence corresponding to segment 20–180 of human TNF-RI (Nophar et al., 1990) and was prepared in CHO cells and provided by Interpharm Laboratories Ltd. (Israel) under the name of r-h TBP-1.

Material. General cell culture material was purchased from Gibco BRL, Life Technologies (Paisley, UK). Estradiol-17β RIA Kit was purchased from DPC (Los Angeles, Calif., USA). Inoketam was purchased from Virbac (Carros, FR). [$^{51}$Cr]-sodium chromate was purchased from NEN Dupont (Boston, Mass., USA). Rompun was purchased from Bayer AG (Leverkusen, DE). Silk suture 7.0 was purchased from Ethicon (Pomezia, IT).

Experimental model of endometriosis in the rat. To explore the effects of the recombinant soluble TNF-RI in endometriosis, a previously described experimental model (Jones, 1987) was used with minor modifications. Under Inoketam/Rompun anaesthesia, an autologous fragment of endometrial tissue (1 cm in length) was resected from the right uterine horn and placed in PBS at 37° C. The uterine segment was opened by a longitudinal incision, and a 5×5 mm section was transplanted, without removing the myometrium, onto the inner surface of the abdominal wall using non-absorbable silk suture at four corners.

Exploration of the study drugs effects in the experimental model of endometriosis. Experimental endometriosis was surgically induced in anaesthetized rats as reported above. In addition, another group of rats similarly had a fragment of one uterine horn removed but a 5×5-mm square of fat surrounding the uterus was transplanted (sham-operated group). One further group of rats, not undergoing any surgical procedure, was kept as a normal control group. Three weeks after the induction of endometriosis, the animals underwent a second laparatomy (pre-treatment laparatomy) to evaluate the size and viability of the ectopic endometrial tissue. The surface area (length×width) was measured using a calliper and recorded. The animals showing viable engraftments were assigned to the designated treatment groups as reported in Table I, so that at the end of the experiment, six animals/group for the first sacrifice time-point and five animals/group for the second sacrifice time-point were obtained. The treatments were started after a 1-week recovery period. The control groups received saline alone; another group received three subcutaneous injections of 2 mg/kg Antide every 3 days with a regimen previously shown to suppress ovarian and hypothalamic activity (Sharpe et al., 1990). A further group received 10 mg/kg recombinant soluble TNF-RI, divided into two daily doses over a 1-week period.

TABLE I

| Endometrium Transplantation | Treatment | Days Of treatment[1] | Days of Sacrifice[1] |
|---|---|---|---|
| No | Saline | 28 through 34 | 36, 43 |
| Sham-operated | Saline | 28 through 34 | 36, 43 |
| Yes | Saline | 28 through 34 | 36, 43 |
| Yes | Antide (2 mg/kg) | 28, 31, 34 | 36, 43 |
| Yes | Recombinant soluble TNF-RI (10 mg/kg in two daily doses) | 28 through 34 | 36, 43 |

[1]From the day of surgical engraftment (day 1).

At the designated sacrifice time-points (2 and 9 days after the last treatment i.e. 36 and 43 days after surgical engraftment), the animals were anaesthetised; blood samples were collected from abdominal aorta, sera were separated and stored at −20° C. until analyzed for estradiol-17β level determination. Spleens were excised for measurement of the Natural Killer (NK) activity. The surface area of endometriosis-like foci were measured at each sacrifice time-point in order to normalize data, the percent variation versus the pre-treatment laparatomy value was calculated by the formula:

$$\frac{(X - X_Q)}{X_Q} \times 100$$

where $X_0$ is the size at time of pre-treatment laparatomy and X is the size at the time of sacrifice. The mean value of percent variation in each group was then computed.

NK activity determination. The extent of NK activity was determined using the $^{51}$Cr-release assay. Murine lymphoma YAC-1 cells were harvested during the exponential growth phase and washed once with medium (RPMI 1640 containing penicillin/streptomycin, L-glutamine and 10% heat-inactivated fetal calf serum). The cell pellet was incubated with 100 μCi of [$^{51}$Cr]-sodium chromate at 37° C., 5% $CO_2$ for 2 hours. Cells were then washed 3 times with 10 ml of assay medium, resuspended at the desired concentration and added to the assay plate in the presence of splenocytes. They were resuspended in assay medium at the desired concentration (2×10$^6$/ml) and serial dilutions were carried out in the assay medium in triplicate wells of a U-bottom 96-well plate prior to the addition of $^{51}$Cr-labelled target cells. $^{51}$Cr-labelled target cells (5×10$^3$) were added to each well of the assay plate and three effector-to-target ratios (200:1, 100:1 and 50:1) were assayed for each sample. The plate containing the effector-to-target cell mixture was centrifuged at 200×g for 4 min and then incubated at 37° C., 5% $CO_2$ for 4 hours. After an additional centrifugation of the plate at 200×g for 4 min, 20 μl of the supernatant from each well was transferred to a glass fiber filter and the associated radioactivity was evaluated by a β-counter.

The percentage of lysis was calculated as follows:

$$\frac{cpm_{sample} - cpm_{spont.}}{cpm_{total} - cpm_{spont.}} \times 100$$

where:
$cpm_{sample}$=mean $^{51}$Cr release in the presence of effector cells
$cpm_{spont.}$=mean $^{51}$Cr release of target cells in the presence of culture medium
$cpm_{total}$=mean $^{51}$Cr release of target cells in the presence of 1% Triton-X100.

Estradiol-17β determination. Serum estradiol-17β concentrations were determined using a commercially available kit to quantify estradiol in serum with no extraction step (DPC, Los Angeles, Calif., USA). Briefly, $^{125}$I-labeled estradiol competes with estradiol in the serum sample for antibody sites. After incubation, separation of bound from free was achieved by decanting. The tube was then counted in a gamma counter (LKB-Pharmacia Wallak), the counts being inversely related to the amount of estradiol present in the serum sample. The quantity of estradiol in the samples was determined by comparing the counts to a calibration curve. The antiserum is highly specific for estradiol, with a relatively low cross-reactivity to other naturally occurring steroids. Samples from the same experimental session were analyzed in a single immunoassay.

Statistical analysis. Statistical significance of the differences observed among the treatment groups was evaluated using the ANOVA present in the Statgraphics Plus™ (Version 1.4). The Tukey's multiple range test (P<0.05) was performed.

Results

Exploration of Recombinant Soluble TNF-RI effects in experimental endometriosis.

Successful growth and development of surgically transplanted endometrial tissue in the rat has offered a research model that has been used to study some of the aspects of endometriosis that cannot be adequately investigated in humans (Dudley et al., 1992). Previous studies in rat experimental endometriosis indicate that Antide works properly as a positive control (Sharpe et al., 1990). In the present invention Antide was compared, in term of dimension of engraftment size before and after treatment, with the ones obtained using recombinant soluble TNF-RI, as summarized in Table II.

TABLE II

| Treatment | Dose (mg/kg) | Observation Time After Last Treatment (day) | Mean ± SEM Pre-treatment values ($cm^2$) | Mean ± SEM Post-treatment values ($cm^2$) |
| --- | --- | --- | --- | --- |
| Saline | — | 2 | 1.45 ± 0.41 | 1.18 ± 0.15 |
| Soluble TNF-RI | 10 | 2 | 1.43 ± 0.38 | 0.77 ± 0.09 |
| Antide | 2 | 2 | 1.43 ± 0.34 | 0.08 ± 0.02 |
| Saline | — | 9 | 1.28 ± 0.24 | 0.97 ± 0.11 |

TABLE II-continued

| Treatment | Dose (mg/kg) | Observation Time After Last Treatment (day) | Mean ± SEM Pre-treatment values ($cm^2$) | Mean ± SEM Post-treatment values ($cm^2$) |
| --- | --- | --- | --- | --- |
| Soluble TNF-RI | 10 | 9 | 1.42 ± 0.38 | 0.54 ± 0.19 |
| Antide | 2 | 9 | 1.41 ± 0.32 | 0.19 ± 0.09 |

Figure 1:
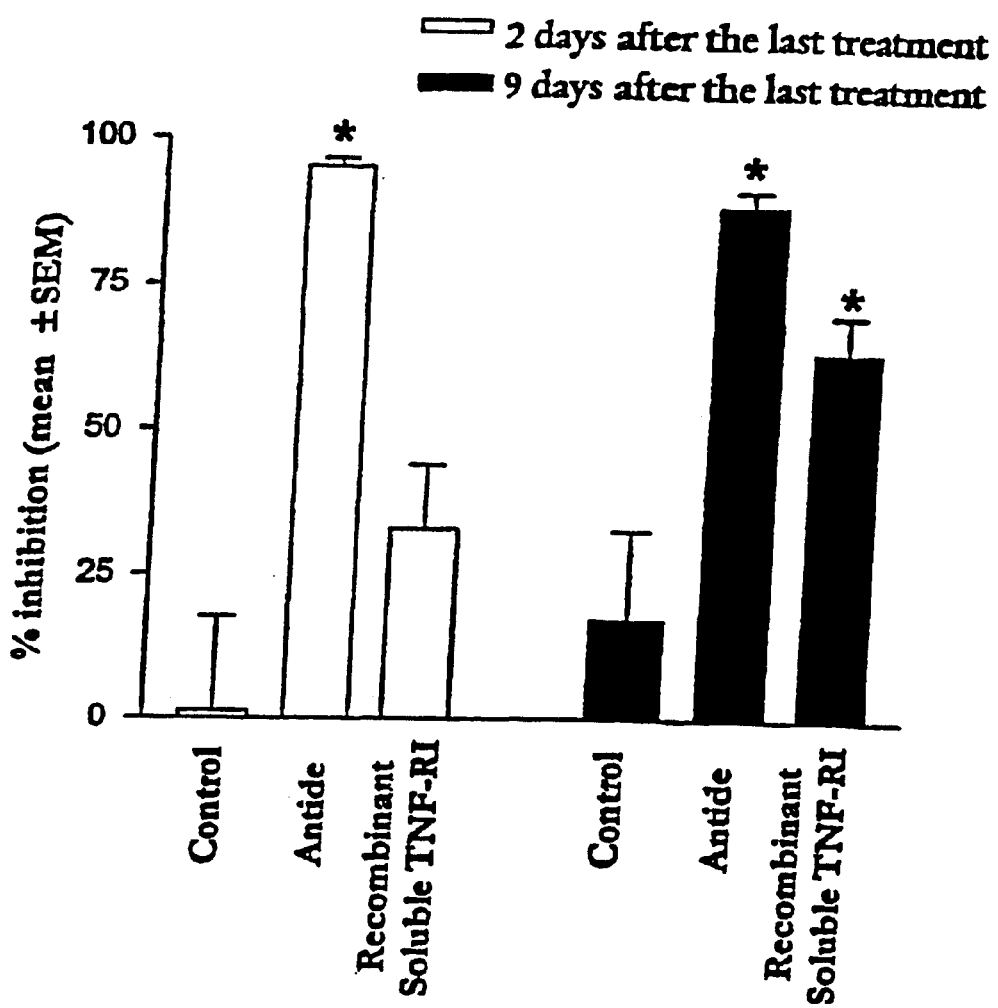

The results are expressed in FIG. 1 as the mean percentage inhibition of engrafted endometrium fragments (calculated as described above).

Antide was effective in reducing the size of the endometriotic-like foci (FIG. 1), inducing an almost complete (94% and 88% compared to the original dimension, respectively) and statistically significant (p<0.05, ANOVA and Tukey's test) remission at both sacrifice time-points after discontinuation of treatment. The 1-week treatment with human recombinant soluble TNF-RI (10 mg/kg, two daily doses) resulted in a significant size reductions (33% and 64% compared to the original dimension, respectively) of the endometriotic-like foci at both observation time-points but statistically significant (p<0.05, ANOVA and Tukey's test) only at day 9. Engraftments were not observed in the sham-operated animals at any time.

NK cell activities evaluation

NK cell activity was evaluated by in vitro tests with spleen cells against YAC cells did not show any difference among groups (FIG. 2), similarly to what has been observed in baboons, where no difference in antiendometrial cytotoxicity and NK cell activity was found in animals with and without endometriosis (D'Hooghe et al., 1995). This finding is in contrast with human data where depressed NK activity in patients with endometriosis has been reported with a significant correlation between reduced peritoneal NK activity and severity of endometriosis (Oosterlynck et al., 1992).

Serum estradiol-17β evaluation

The serum estradiol-17β concentrations were measured by radioimmunoassay at both sacrifice time-points. A significant difference was observed in the Antide-treated groups as compared to the untreated controls at the second observation time-point. No statistical significant differences were observed for recombinant soluble TNF-RI when compared to controls (FIG. 3; p<0.05, ANOVA and Tukey's test).

Conclusions

In the rat experimental model of endometriosis, administration of a TNF antagonist, the soluble form of TNF-RI, provides, for the first time, a clear evidence of the potential effectiveness of cytokine-based, non hormone-related treatment of this pathological condition. Thus, TNF antagonists represent an alternative to the existing medical treatments in terms of reduced side effects. These results assess the use of TNF antagonists in the treatment of endometriosis-related infertility.

Those skilled in the art will know, or be able to ascertain, using no more than routine experimentation, many equivalents to the specific embodiments of the inventions described herein. These and all other equivalents are intended to be encompassed by the following claims.

Reference List

Arici, A., Tazuke, S. I., Attar, E., Kliman, H. J., and Olive, D. L., 1996a, Mol.Hum.Reprod. 2, 40–45.
Arici, A., Oral, E., Bukulmez, O., Duleba, A., Olive, D. L., and Jones, E. E., 1996b, Fertil.Steril. 65, 603–607.

Arici, A., Oral, E., Attar, E., Tazuke, S. I., and Olive, D. L., 1997, Fertil.Steril. 67, 1065–1072.

Barbieri, R. L., 1988, N.Engl.J.Med. 318, 512–514.

Bazzoni, F. and Beutler, B., 1996, N.Engl.J.Med. 334, 1717–1725.

Cheung, A. N., 1996, Curr.Opin.Obstet.Gynecol. 8, 46–51.

D'Hooghe, T. M., Scheerlinck, J. P., Koninckx, P. R., Hill, J. A., and Bambra, C. S., 1995, Hum.Reprod. 10, 558–562.

Dawood, M. Y., 1993, Int. J.Gynaecol.Obstet. 40 (Suppl.), S29–42.

Dudley, D. J., Hatasaka, H. H., Branch, D. W., Hammond, E., and Mitchell, M. D., 1992, Am.J.Obstet.Gynecol. 167, 1774–1780.

Eisermann, J., Gast, M. J., Pineda, J., Odem, R. R., and Collins J. L., 1988, Fertil.Steril. 50, 573–579.

Eisermann, J., Register, K. B., Strickler R. C., and Collins J. L., 1989, J.Androl. 10, 270–274.

Elliott, M. J., Maini, R. N., Feldmann, M., Long-Fox, A., Charles, P., Bijl, H., and Woody, J. N., 1994, Lancet 344, 1125–1127.

Engelmann, H., Novick, D., and Wallach, D., 1990, J.Biol.Chem. 265, 1531–1536.

Fiers, W., 1991, FEBS Lett. 285, 199–212.

Gray, P. W., Aggarwal, B. B., Benton, C. V., Bringman, T. S., Henzel, W. J., Jarrett, J. A., Leung, D. W., Moffat, B., Ng, P., and Svedersky, L. P., 1984, Nature 312, 721–724.

Hahn, D. W., Carraher, R. P., Foldesy, R. G., and McGuire, J. L., 1986, Am.J.Obstet.Gynecol. 155, 1109–1113.

Halme, J., 1991, Ann.N.Y.Acad.Sci. 622, 266–274.

Harada, T., Yoshioka, H., Yoshida, S., Iwabe, T., Onohara, Y., Tanikawa, M., and Terakawa, N., 1997, Am.J.Obstet.Gynecol. 176, 593–597.

Ho, H. N., Wu, M. Y., and Yang, Y. S., 1997, Am.J.Reprod.Immunol. 38, 400–412.

Hornung, D., Ryan, I. P., Chao, V. A., Vigne, J. L., Schriock, E. D., and Taylor, R. N., 1997, J.Clin.Endocrinol.Metab. 82, 1621–1628.

Hunt, J. S., Chen, H. L, Hu, X. L., and Tabibzadeh, S., 1992, Biol.Reprod. 47, 141–147.

Jones, R. C., 1987, Acta Endocrinol.(Copenh.) 114, 379–382.

Knight, D. M., Trinh, H., Le, J., Siegel, S., Shealy, D., McDonough, M., Scallon, B., Moore, M. A., Vilcek, J., and Daddona, P., 1993, Mol.Immunol. 30, 1443–1453.

Koninckx, P. R., Meuleman, C., Demeyere, S., Lesaffre, E., and Cornillie, F. J., 1991, Fertil.Steril. 55, 759–765.

Koninckx, P. R. and Martin, D., 1994, Curr.Opin.Obstet.Gynecol. 6, 231 . 241.

MacSween, R. N. M., 1993, Muir's Textbook of pathology, 13th ed. (Whaley K.; ISBN 0-340-55145-3), 1024–1025.

Malinak, L. R., Buttram, V. C. J., Elias, S., and Simpson, J. L., 1980, Am.J.Obstet.Gynecol. 137, 332–337.

Matalliotakis, I., Neonaki, M., Zolindaki, A., Hassan, E., Georgoulias, V., and Koumantakis, E., 1997, Int.J.Fertil.Womens.Med. 42, 211–214.

Mori, H., Nakagawa, M., Itoh, N., Wada, K., and Tamaya, T., 1990, Am.J.Reprod.Immunol. 24, 45–50.

Nophar, Y., Kemper, O., Brakebusch, C., Englemann, H., Zwang, R., Aderka, D., Holtmann, H., and Wallach, D., 1990, EMBO J. 9,3269–3278.

Oosterlynck, D. J., Meuleman, C., Waer, M., Vandeputte, M., and Koninckx, P. R., 1992, Fertil.Steril. 58, 290–295.

Overton, C., Fernandez-Shaw, S., Hicks, B., Barlow, D., and Starkey, P., 1996, Hum.Reprod. 11, 380–386.

Pennica, D., Nedwin, G. E., Hayflick, J. S., Seeburg, P. H., Derynck, R., Palladino, M. A., Kohr, W. J., Aggarwal, B. B., and Goeddel, D. V., 1984, Nature 312, 724–729.

Rana, N., Braun, D. P., House, R., Gebel, H., Rotman, C., and Dmowski, W. P., 1996, Fertil.Steril. 65, 925–930.

Revelli, A., Modotti, M., Ansaldi, C., and Massobrio, M., 1995, Obstet.Gynecol.Surv. 50, 747–754.

Roby, K. F., Laham, N., and Hunt, J. S., 1996, J.Reprod. Fertil. 106, 285–290.

Shalaby, M. R., Laegreid, W. W., Ammann, A. J., and Liggitt, H. D., 1989, Lab.Invest. 61, 564–570.

Shalaby, M. R., Sundan, A., Loetscher, H., Brockhaus, M., Lesslauer, W., and Espevik, T., 1990, J.Exp.Med. 172, 1517–1520.

Sharpe, K. L., Bertero, M. C., and Vernon, M. W., 1990, Prog.Clin.Biol.Res. 323, 449–58

Tucci, A., James, H., Chicheportiche, R., Bonnefoy, J. Y., Dayer, J. M., and Zubler, R. H., 1992, J.Immunol. 148, 2778–2784.

Waller, K. G. and Shaw, R. W., 1993, Fertil.Steril. 59, 511–515.

Zhang, R. J., Wild, R. A., and Ojago, J. M., 1993, Fertil.Steril. 59, 1196–1201.

What is claimed is:

1. A method for treating endometriosis, comprising administering to a patient in need thereof a therapeutically effective amount of sequestering antagonist.

2. The method of claim 1, wherein said TNF sequestering antagonist is a receptor molecule, derivative or a fragment thereof which binds to TNF.

3. The method of claim 1, wherein said TNF sequestering antagonist is an anti-TNF antibody or a fragment thereof.

4. A method for improving implantation and fertility rate by reducing endometriotic lesions, comprising administering to a patient in need thereof a therapeutically effective amount of a TNF sequestering antagonist.

5. The method of claim 4, wherein said TNF sequestering antagonist is a receptor molecule, derivative or a fragment thereof which binds to TNF.

6. The method of claim 4, wherein said TNF sequestering antagonist is an anti-TNF antibody or a fragment thereof.

* * * * *

UNITED STATES PATENT AND TRADEMARK OFFICE
CERTIFICATE OF CORRECTION

| | | |
|---|---|---|
| PATENT NO. | : 6,663,865 B1 | Page 1 of 1 |
| DATED | : December 16, 2003 | |
| INVENTOR(S) | : Francesco Borrelli, Mauro D'Antonio and Fabrizio Martelli | |

It is certified that error appears in the above-identified patent and that said Letters Patent is hereby corrected as shown below:

Column 14,
Line 37, after "amount of" insert -- a TNF --.

Signed and Sealed this

Twelfth Day of October, 2004

JON W. DUDAS
*Director of the United States Patent and Trademark Office*